United States Patent [19]

Fosco et al.

[11] Patent Number: 5,509,935
[45] Date of Patent: Apr. 23, 1996

[54] INTRAMEDULLARY IMPLANT WITH OPTIMIZED GEOMETRIC STIFFNESS

[75] Inventors: Dominic R. Fosco; R. Steven Boggan, both of Cordova, Tenn.

[73] Assignee: Wright Medical Technology, Inc., Arlington, Tenn.

[21] Appl. No.: 194,284

[22] Filed: Feb. 16, 1994

[51] Int. Cl.$^6$ .................................................. A61F 2/32
[52] U.S. Cl. ........................... 623/22; 623/11; 623/16; 623/18
[58] Field of Search .................... 623/11, 16, 18, 623/22, 23; 606/62, 63, 67

[56] References Cited

U.S. PATENT DOCUMENTS

| | | | |
|---|---|---|---|
| 3,996,625 | 12/1976 | Noiles | 623/18 |
| 4,795,472 | 1/1989 | Crowninshield et al. | 623/18 |
| 4,921,501 | 5/1990 | Glacometti | 623/18 |
| 5,108,450 | 4/1992 | Horber et al. | 623/23 |
| 5,316,550 | 5/1994 | Forte | 623/23 |
| 5,336,265 | 8/1994 | Serbousek et al. | 623/23 |

*Primary Examiner*—Randall L. Green
*Assistant Examiner*—P. Zuttarelli
*Attorney, Agent, or Firm*—Walker, McKenzie & Walker

[57] ABSTRACT

An intramedullary implant including an elongated body, a first groove in the body for varying the geometric stiffness of the body; and a second groove in the body for varying the geometric stiffness of the body. The first and second groove have varying cross-sectional shapes whereby the geometric stiffness of the body can be optimized.

20 Claims, 2 Drawing Sheets

INTRAMEDULLARY IMPLANT WITH OPTIMIZED GEOMETRIC STIFFNESS

BACKGROUND OF THE INVENTION

1. Field of the Invention

The present invention relates, in general, to an intramedullary implant having an elongated body specifically designed so that the geometric stiffness thereof can be optimized.

2. Information Disclosure Statement

Stiffness of an implant is determined by both material and geometry. Materials of choice for implant devices are titanium alloy, cobalt-chrome alloy and 316L stainless steel with titanium alloy having one-half the stiffness of the later materials. Consequently, a designer is limited as to the effect of material on stem stiffness. The geometry of a device has a major impact on intramedullary implant stiffness. Hereafter, the effect of geometry on intramedullary implant stiffness shall be referenced to as geometric stiffness. Various intramedullary implants have previously been designed so that the flexibility or stiffness of the implant can be varied. A preliminary patentability search produced the following patents that appear to be relevant to the present invention:

Smith, U.S. Pat. No. 5,007,931, issued Apr. 16, 1991, discloses a porous coated prosthesis including an elongated stem member intended for cementless fixation in the medullary canal of a long bone. The stem member has one or more longitudinally extending channels. A porous medium for enabling and encouraging bone in growth is bonded to the bottom surface of each channel but is free of the sidewalls of the channels. The longitudinal channels are also disclosed as reducing the section modulus of the stem, to make the stem more flexible. The Smith patent teaches that the depth of the longitudinal channels "may be of any dimensions suitable for a particular implant."

Giacometti, U.S. Pat. No. 4,921,501, issued May 1, 1990, discloses a stem for a femoral prosthesis including a distal end having a cylindrical cross section. The resiliency of the stem increases distally due to a hollow formed in the distal end of the stem either by a series of stepped bores as shown in FIGS. 1 and 2c–2f, or by a constant diameter bore that extends angularly of the longitudinal axis of the stem as shown in FIGS. 3 and 4c–4f. The distally increasing resilience of the stem is due to the increasing decrease in the lateral wall thickness or total cross-sectional area.

Smith, U.S. Pat. No. 4,808,186, issued Feb. 28, 1989, discloses a femoral prosthesis having an elongated stem for insertion in the intramedullary canal of a femur. The stem has a longitudinal channel therein which lies generally in the coronal plane when the stem is implanted. The thickness of the stem laterally of the channel is variable between the proximal and distal ends to affect the moment of inertial at any given location along the length of the stem to thereby provide stem flexibility that substantially correlates to the flexibility of the bone.

Petrtyl et al., U.S. Pat. No. 4,743,263, issued May 10, 1988, discloses a hip prosthesis including a shaft for being implanted in a femur. The shaft is composed of at least two, spirally twisted elastic rods. The elastic rods have a "turn" larger than the diameter of the prepared cavity in the femur so that the elastic rods are stressed when inserted into the prepared cavity. The elastic rods may have a variable cross section.

Forte, U.S. Pat. No. 5,092,899, issued Mar. 3, 1992, discloses a prosthesis with an intramedullary stem that has flexibility comparable to that of the surrounding bone. A bore is disposed in the stem portion with the stem wall thickness uniform or varying from the proximal end to the distal end, depending upon the amount of flexibility wanted. The stiffness along the length of the stem may additionally be varied by varying the depth of the bore into the stem.

Farling, U.S. Pat. No. 4,997,444, issued Mar. 5, 1991, discloses a hip prosthesis having a stem constructed so that the modulus of elasticity thereof vary from one end to the other. The stem includes a plurality of alternating solid and mesh discs stacked one on top of the other with the relationship between the composite thickness of mesh and solid discs determining the modulus of elasticity at any region thereof.

Hofmann, U.S. Pat. 4,936,863, issued Jun. 26, 1990, discloses a hip prosthesis including a femoral component having an upwardly and laterally open slot formed in an upper region thereof to allow compression of the femoral component for easier installation into a resected femur. An antirotation fin can be inserted into the slot after the femoral component is implanted to prevent rotation of the femoral component and maintain the femoral component in an expanded state.

Pappas et al., U.S. Pat. No. 5,030,234, issued Jul. 9, 1991, discloses a femoral hip prosthesis including a stem and an extension for being connected to the distal end of the stem by a slip fit connection that reduces surface tensile forces in regions of the prosthesis adjacent the interface between the stem and the extension.

Tepic, PCT publication WO 89/01321, published Feb. 23, 1989, discloses a stem for a hip prosthesis having a central region provided with a regular pattern of anteroposterior cuts extending from the proximal regions of the stem to the distal end of the stem, rendering the stem stiffness adaptable to the stiffness of the receiving bone cavity.

Nothing in the known prior art discloses or suggests the present invention. More specifically, nothing in the known prior art discloses or suggests an intramedullary implant including an elongated body for being implanted in the medullary canal of a long bone, a first groove means for varying the geometric stiffness of the body, and a second groove for varying the geometric stiffness of the body, the first and second groove means having contours with varying cross-sectional shapes whereby the geometric stiffness of the body can be optimized.

SUMMARY OF THE INVENTION

The present invention provides an intramedullary implant having an elongated body specifically designed so that the geometric stiffness thereof can be optimized. A basic concept of the present invention is to progressively vary the stiffness along the length of an elongated body member of an intramedullary implant by, for example, providing a plurality of longitudinally extending grooves in the outer surface of the body member and varying the depth of the grooves along the length of the body member to progressively vary the stiffness of the stem member along the length thereof.

The improved implant of the present invention includes, in general, an elongated intramedullary body for being implanted in the medullary canal of a long bone, a first groove means for varying the geometric stiffness of the body, and a second groove for varying the geometric stiffness of the body, the first and second groove means having contours with varying cross-sectional shapes whereby the geometric stiffness of the body can be optimized.

One object of the present invention is to provide an improved intramedullary implant that allows the stiffness of the body thereof to be tailored to the stiffness of the natural bone into which the body is being implanted.

Another object of the present invention is to reduce any pain felt by an implant patient that might be caused by the implant being stiffer than the natural bone being repaired or replaced.

DESCRIPTION OF THE PREFERRED EMBODIMENTS

Figure 1:
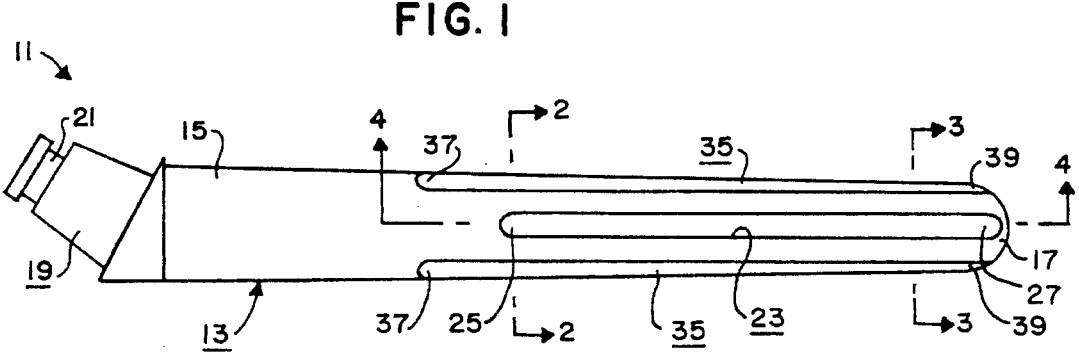
FIG. 1 is a side elevational view of a first embodiment of an intramedullary implant of the present invention.
Figure 2:
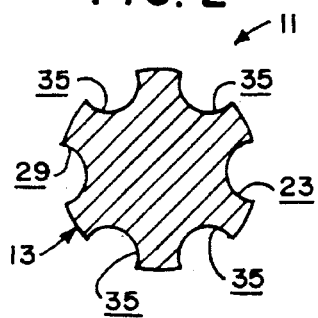
FIG. 2 is a sectional view substantially as taken on line 2—2 of FIG. 1 on an enlarged scale.
Figure 3:
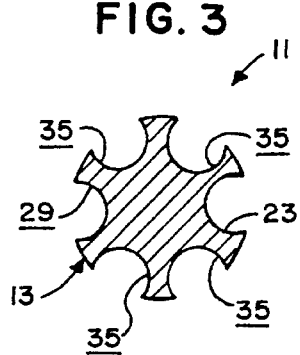
FIG. 3 is a sectional view substantially as taken on line 3—3 of FIG. 1 on an enlarged scale.
Figure 4:
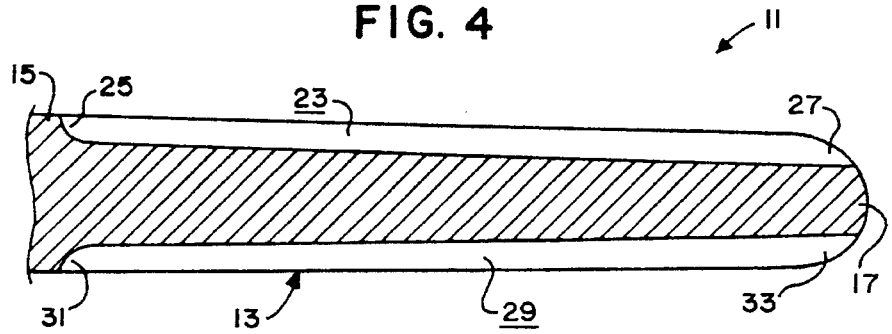
FIG. 4 is a sectional view substantially as taken on line 4—4 of FIG. 1 on an enlarged scale.

A first preferred embodiment of the intramedullary implant of the present invention is shown in FIGS. 1–4, and identified by the numeral 11. The intramedullary implant 11 is especially designed to allow the geometric stiffness thereof to be varied and optimized.

The intramedullary implant 11 includes an elongated body or body member 13 having a first end 15 and a second end 17. The intramedullary implant 11 may consist of a modular femoral stem prosthesis having an angled male taper or neck 19 on the first end 15 of the body 13 for being removably coupled to a femoral head prosthesis (not shown) as will now be apparent to those skilled in the art. The neck 19 may have an extraction groove 21 or the like thereon to facilitate removal of the body 13, should it become necessary.

A first groove means 23 is provided in the body 13 for varying the geometric stiffness of the body 13. The first groove means 23 may consist of an elongated flute or notch in the outer surface of the body 13 extending generally between the first and second ends 15, 17 thereof. Thus, the first groove means 23 has a first end 25 located toward the first end 15 of the body 13 and a second end 27 located toward the second end 17 of the body 13.

A second groove means 29 is provided in the body 13 for varying the geometric stiffness of the body 13. The second groove means 29 may consist of an elongated flute or notch in the outer surface of the body 13 extending generally between the first and second ends 15, 17 thereof. Thus, the second groove means 29 preferably has a first end 31 located toward the first end 15 of the body 13 and a second end 33 located toward the second end 17 of the body 13.

A critical feature of the present invention is that the first and second groove means 23, 29 have contours with varying cross-sectional shapes whereby the geometric stiffness of the body member 13 can be optimized. In the embodiment shown in FIGS. 1–4, the depth of the first groove means 23 varies between the first and second ends 25, 27 thereof and the depth of the second groove means 29 varies between the first and second ends 31, 33 thereof. Thus, for example, the depth of the first groove means 23 is preferably greater at the second end 27 thereof that at the first end 25 thereof as clearly illustrated in FIGS. 2–4. Also, the depth of the second groove means 29 is preferably greater at the second end 33 thereof that at the first end 31 thereof. Such a construction causes the geometric stiffness of the body 13 to be progressively less at the second end 17 thereof that at the first end 15 thereof as will now be apparent to those skilled in the art.

Additional groove means 35 may be provided in the body 13 for varying the geometric stiffness of the body 13. Each additional groove means 35 may consist of an elongated flute or notch in the outer surface of the body 13 extending generally between the first and second ends 15, 17 thereof. Thus, each additional groove means 35 has a first end 37 located toward the first end 15 of the body 13 and a second end 39 located toward the second end 17 of the body 13. The depth of each additional groove means 35 is preferably greater at the second end 37 thereof that at the first end 39 thereof. Such a construction causes the geometric stiffness of the body 13 to be progressively less at the second end 17 thereof that at the first end 15 thereof.

The geometric stiffness of the body 13 can be optimized by varying the number, location, length, width and/or diameter of the groove means, etc. The depth of the groove means can be altered in order to provide a progressive change in stiffness along the length of the body 13. Furthermore, the location, length, width and/or diameter of the groove means can be staggered or arranged so as to avoid potential stress concentration and/or to allow the geometric stiffness of the body 13 to be optimized at desired sections or segments thereof. For example, the first ends 37 of the groove means 35 are shown in FIG. 1 as starting at a point closer to the first end 15 of the body 13 than the first end 25 of the groove means 23 (i.e., the first ends 37, 25 of the groove means 35, 23 are staggered with respect to one another).

The intramedullary implant 11 can be constructed in various specific manners out of various specific materials as will now be apparent to those skilled in the art. For example, the intramedullary implant 11 can be machined or otherwise formed out of titanium alloy, cobalt-chrome alloy or 316L stainless steel, etc. While the intramedullary implant 11 is herein discloses and shown as a femoral stem prosthesis, it could also be designed as a tibial stem, a fracture fixation rod, etc.

Figure 5:
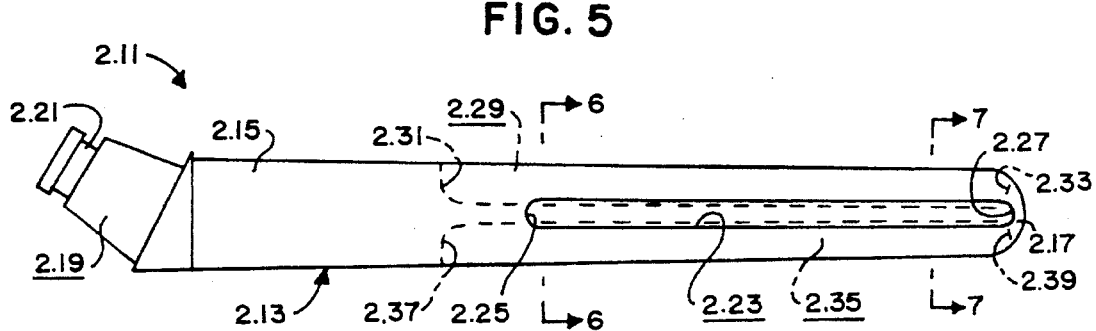
FIG. 5 is a side elevational view of a second embodiment of an intramedullary implant of the present invention.
Figure 6:
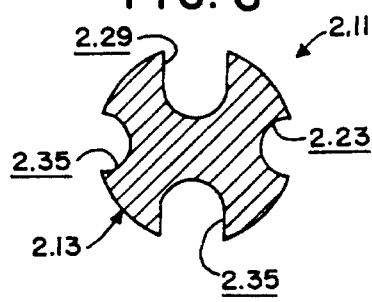
FIG. 6 is a sectional view substantially as taken on line 6—6 of FIG. 5 on an enlarged scale.
Figure 7:
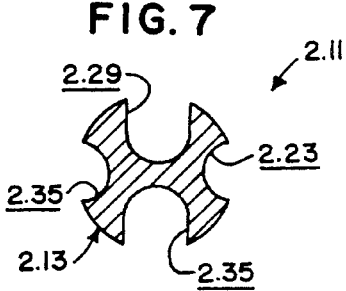
FIG. 7 is a sectional view substantially as taken on line 7—7 of FIG. 5 on an enlarged scale.

A second preferred embodiment of the intramedullary implant of the present invention is shown in FIGS. 5–7, and identified by the numeral 2.11. The intramedullary implant 2.11 is especially designed to allow the geometric stiffness thereof to be varied and optimized.

The intramedullary implant 2.11 includes an elongated body or body member 2.13 having a first end 2.15 and a second end 2.17. The intramedullary implant 2.11 may consist of a modular femoral stem prosthesis having an angled male taper or neck 2.19 on the first end 2.15 of the body 2.13 for being removably coupled to a femoral head prosthesis (not shown) as will now be apparent to those skilled in the art. The neck 2.19 may have an extraction groove 2.21 or the like thereon to facilitate removal of the body 2.13, should it become necessary.

A first groove means 2.23 is provided in the body 2.13 for varying the geometric stiffness of the body 2.13. The first groove means 2.23 may consist of an elongated flute or notch in the outer surface of the body 2.13 extending generally between the first and second ends 2.15, 2.17 thereof. Thus, the first groove means 2.23 has a first end 2.25 located toward the first end 2.15 of the body 2.13 and a second end 2.27 located toward the second end 2.17 of the body 2.13.

A second groove means 2.29 is provided in the body 2.13 for varying the geometric stiffness of the body 2.13. The second groove means 2.29 may consist of an elongated flute or notch in the outer surface of the body 2.13 extending generally between the first and second ends 2.15, 2.17 thereof. Thus, the second groove means 2.29 preferably has a first end 2.31 located toward the first end 2.15 of the body 2.13 and a second end 2.33 located toward the second end 2.17 of the body 2.13.

A critical feature of the present invention is that the first and second groove means 2.23, 2.29 have contour with varying cross-sectional shapes whereby the geometric stiffness of the body member 2.13 can be optimized. In the embodiment shown in FIGS. 5.7, the depth and width of the first groove means 2.23 is less than the depth and width of the second groove means 2.29.

Additional groove means 2.35 may be provided in the body 2.13 for varying the geometric stiffness of the body 2.13. Each additional groove means 2.35 may consist of an elongated flute or notch in the outer surface of the body 2.13 extending generally between the first and second ends 2.15, 2.17 thereof. Thus, each additional groove means 2.35 has a first end 2.37 located toward the first end 2.15 of the body 2.13 and a second end 2.39 located toward the second end 2.17 of the body 2.13. As shown in FIGS. 6 and 7, an additional groove means 2.35 may be provided opposite the first groove means 2.23 and another additional groove means 2.35 may be provided opposite the second groove means 2.29, with the additional groove means 2.35 opposite the first groove means 2.35 preferably being a mirror image of the first groove means 2.35 and with the additional groove means 2.35 opposite the second groove means 2.29 preferably being a mirror image of the second groove means 2.29.

The geometric stiffness of the body 2.13 can be optimized by varying the number, location, length, width and/or diameter of the groove means, etc. The depth of the groove means can be altered in order to provide a progressive change in stiffness along the length of the body 2.13. Furthermore, the location, length, width and/or diameter of the groove means can be staggered or arranged so as to avoid potential stress concentration and/or to allow the geometric stiffness of the body 2.13 to be optimized at desired sections or segments thereof. For example, the first end 2.37 of the groove means 2.35 is shown in FIG. 5 as starting at a point closer to the first end 2.15 of the body 2.13 than the first end 2.25 of the groove means 2.23 (i.e., the first ends 2.37, 2.25 of the groove means 2.35, 2.23 are staggered with respect to one another).

The intramedullary implant 2.11 can be constructed in various specific manners out of various specific materials as will now be apparent to those skilled in the art. For example, the intramedullary implant 2.11 can be machined or otherwise formed out of titanium alloy, cobalt-chrome alloy or 316L stainless steel, etc. While the intramedullary implant 2.11 is herein discloses and shown as a femoral stem prosthesis, it could also be designed as a tibial stem, a fracture fixation rod, etc.

Although the present invention has been described and illustrated with respect to preferred embodiments and preferred uses therefor, it is not to be so limited since modifications and changes can be made therein which are within the full intended scope of the invention.

We claim:

1. An intramedullary implant comprising an elongated body member having a first end and a second end and having a geometric stiffness; first groove means in said body member extending between said first and second ends of said body member for varying the geometric stiffness of said body member; and second groove means in said body member extending between said first and second ends of said body member a greater distance than said first groove means for varying the geometric stiffness of said body member; said first and second groove means being disconnected from one another and having contours; said contour of said first groove means having a cross-sectional area; said contour of said second groove means having a cross-sectional area; said cross-sectional area of said contour of said first groove means being different than said cross-sectional area of said contour of said second groove means for allowing the geometric stiffness of said body member to be optimumly varied.

2. The intramedullary implant of claim 1 in which said first groove means has a greater depth than said second groove means.

3. The intramedullary implant of claim 1 in which said first groove means has a greater width than said second groove means.

4. The intramedullary implant of claim 1 in which said first groove means has a greater depth and width than said second groove means.

5. The intramedullary implant of claim 1 in which said first groove means has a first end and a second end; and in which the depth of said first groove means varies between said first and second end.

6. The intramedullary implant of claim 5 in which said second groove means has a first end and a second end; and in which the depth of said second groove means varies between said first and second end.

7. The intramedullary implant of claim 1 in which said first groove means has a first end and a second end; and in which the cross sectional shape of said contour of said first groove means progressively varies between said first and second end for progressively varying the geometric stiffness of said body member.

8. The intramedullary implant of claim 1 in which said first and second groove means are staggered relative to one another.

9. The intramedullary implant of claim 1 in which said cross-sectional area of said contour of said first groove means is a different shape than said cross-sectional area of said contour of said second groove means.

10. The intramedullary implant of claim 1 in which said cross-sectional area of said contour of said first groove means is a different size than said cross-sectional area of said contour of said second groove means.

11. The improved intramedullary implant of claim 12 in which said first groove means has a greater depth than said second groove means.

12. An improved intramedullary implant including an elongated body member for being implanted in the medullary canal of a bone, said body member having an outer surface, a first end and a second end and having a geometric stiffness; wherein the improvement comprises varying the geometric stiffness of said body member between said first and second ends thereof by providing a first groove means in said body member between said first and second ends of said body member; providing a second groove means in said body member between said first and second ends of said body member; providing a third groove means in said body member between said first and second ends of said body member; and providing a fourth groove means in said body member between said first and second ends of said body member; said groove means being disconnected from one another and having contours; said contour of each of said groove means having a cross-sectional area; said cross-sectional area of said contour of said first groove means being different than said cross-sectional area of said contour of said second groove means for allowing the geometric stiffness of said body member to be optimumly varied; said cross-sectional area of said contour of said third groove means being different than said cross-sectional area of said contour of said fourth groove means for allowing the geometric stiffness of said body member to be optimumly varied.

13. The intramedullary implant of claim 1 in which said cross-sectional area of said contour of said first groove means is a different size and shape than said cross-sectional area of said contour of said second groove means.

14. The improved intramedullary implant of claim 12 in which said first groove means has a greater width than said second groove means.

15. The improved intramedullary implant of claim 12 in which said first groove means has a greater depth and width than said second groove means.

16. The improved intramedullary implant of claim 12 in which said first groove means has a first end and a second end; and in which the depth of said first groove means varies between said first and second end.

17. The improved intramedullary implant of claim 16 in which said second groove means has a first end and a second end; and in which the depth of said second groove means varies between said first and second end.

18. The improved intramedullary implant of claim 12 in which said cross-sectional area of said contour of said first groove means is a different shape than said cross-sectional area of said contour of said second groove means.

19. The improved intramedullary implant of claim 12 in which said cross-sectional area of said contour of said first groove means is a different size than said cross-sectional area of said contour of said second groove means.

20. The improved intramedullary implant of claim 12 in which said cross-sectional area of said contour of said first groove means is a different size and shape than said cross-sectional area of said contour of said second groove means.

* * * * *